Oct. 14, 1947. E. C. OHL Plant Pat. 765
APPLE TREE
Filed Oct. 25, 1946
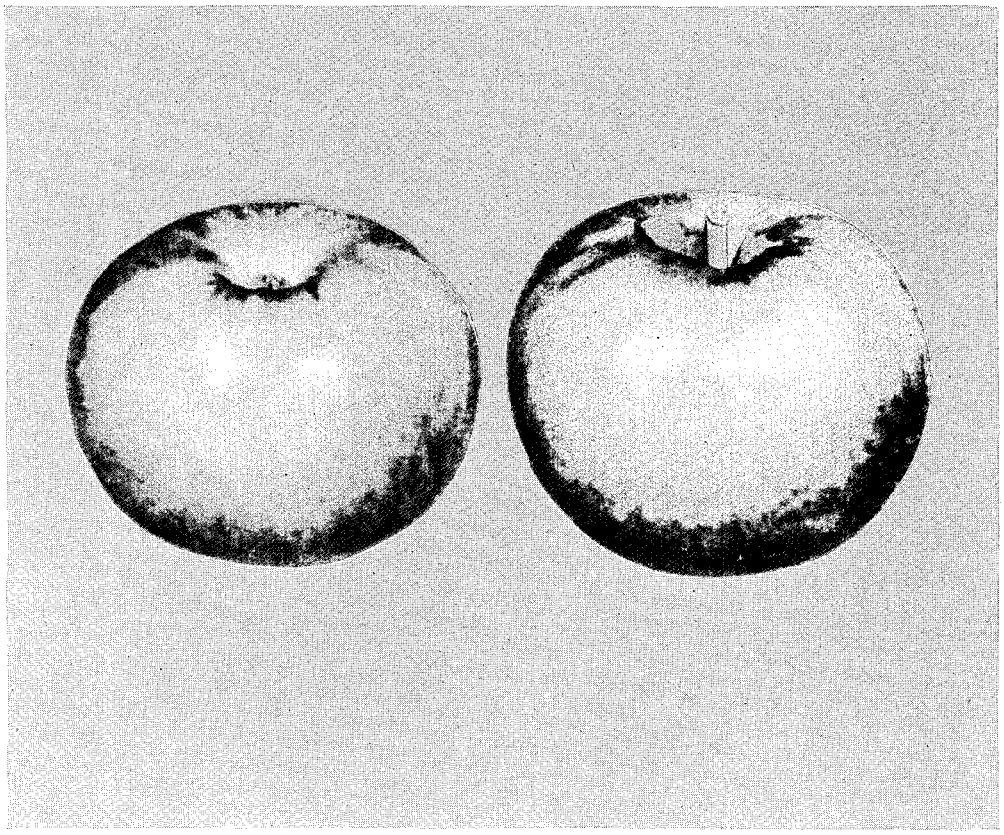
Inventor
E. C. Ohl
By Robb & Robb
Attorneys Patented Oct. 14, 1947

Plant Pat. 765

UNITED STATES PATENT OFFICE

765

APPLE TREE

Earl C. Ohl, Findlay, Ohio, assignor to Stark Bro's Nurseries and Orchards Company, Louisiana, Mo., a corporation of Missouri Application October 25, 1946, Serial No. 705,609

1 Claim. (Cl. 47—62)

The present invention or discovery relates to a new and distinct variety of apple tree, originating as a chance seedling, most nearly resembling, as to certain characteristics, the variety well known to the trade under the name "Wealthy."

From extensive tests, it has been determined that this new variety resembles "Wealthy" in respect to size and shape as well as flavor and texture of the flesh and its eating and cooking qualities where the two varieties referred to are grown under comparable conditions.

Its primary points of distinction, however, reside in its deeper and more attractive red color when fully ripe and its habit of ripening about forty days before the variety "Wealthy," or at about the same ripening season of the variety "Yellow Transparent."

The drawing illustrates specimens of the new variety in obverse positions and depicts the attractive red coloring thereof when fully ripe or at its eating stage.

Asexual reproduction shows that these characteristics hold true through succeeding propagations.

The following is a detailed description of the new variety, giving color designations according to the conventional dictionary definition of terminology as well as corresponding color terms according to Ridgway's Color Chart.

Dates first and last picking: July 3–July 13.

*Tree*

Medium size; vigorous; upright; dense; round topped; rapid growing; hardy; productive; regular bearer.

Trunk: Medium stocky; medium smooth.

Branches: Medium thick; smooth; much branching; Greyish Olive, Ridgway Plate XLVI, Color 21''''. *Lenticels*—medium number; medium size; prominent.

Leaves:

*Length.*—2¾'' to 3½''.

*Width.*—1¾'' to 2½''. Medium size; medium wide; medium long; oval; taper-pointed; medium thick; Elm Green, Ridgway Plate XVII, Color 27', Tone M; rugose.

*Margin.*—Coarsely serrate.

*Petiole.*—Length, 1'' to 1½''; short; medium thick.

Flowers: Dates of first and full bloom—March 29, 1946, April 6, 1946. Medium early compared with other varieties; medium large; pink.

Fruit: Maturity when described—eating ripe, July 10, 1945.

*Size.*—Variable. Axial diameter, 2''. Transverse, 2½''. Oblate.

*Cavity.*—Symmetrical at base; rounded; acute toward base. Breadth, ⅞''. Markings, russeted.

*Basin.*—Symmetrical at base; rounded; base wide; furrowed; pubescent. Depth, $\frac{5}{16}$''. Breadth, $\frac{7}{16}$''.

*Stem.*—Medium slender; pubescent. Length, ½''–1''. Breadth, ⅛''.

*Calyx.*—Closed; segments persistent; length, ¼''; approximate at base; erect; converged from base toward center; connivent; outer surface pubescent; stamens, marginal; calyx tubes, long, broad, funnel-shaped.

*Skin.*—Thin, tough; smooth; glossy. Dots—conspicuous; many; small; even; circular. Color of dots—Gray (Smoke Gray, Ridgway, Plate XLVI, Color 21'''', Tone *d*). Distribution of dots—most numerous at apex. Ground color—Light Viridine Yellow (Ridgway, Plate V, Color 29, Tone *d*). Color Markings—Splashed; bright. Color of markings—Pomegranate Purple (Ridgway, Plate XII, Color 71, Tone 1) grading to Bordeaux (Ridgway, Plate XII, Color 71, Tone K). Bloom—wanting. Scarf-skin—wanting. General color effect—brilliant deep red.

*Flesh.*—Juicy. Color of flesh—satiny; white with yellowish-greenish tint, tinged with red in cortex near skin in some specimens. Texture—firm; tender; granular; crisp. Flavor—subacid; sprightly rich. Aroma—distinct. Quality—Good to best.

*Core.*—Median. Bundle area—medium size; cordate; symmetrical. Halves of area—unequal. Bundles—green yellowish tinge, conspicuous in two whorls. Alternate bundle—distant from tube; reaches tube above stamens. Core lines—meeting; in cross section indistinct. Carpellary area—distinct; small. Calyx-tube—glabrous; cone-shaped. Stem of funnel—short. Styles—present; united; glabrous throughout. Stamens—in one obscure whorl. Axillary cavity—wanting. Seed cells—axile; closed. cell walls—approximate; thin; tough. Length, 0.3''; breadth, .15''. Longitudinal section—broadly ovate; obtuse at apex. Surface—Entire tufted. Cross section—broad.

Seeds:

*Number perfect.*—7–8; imperfect, 0–2.

*Number in one cell.*—Two; length, 0.3″; breadth, 0.2″.

*Color.*—Hazel (Ridgway, Plate XIV, Color 11′, Tone K).

Use: Market; local; culinary.

Keeping quality: Medium.

Resistance:

*To Insects.*—Medium.

*To Diseases.*—Good.

I claim:

A new and distinct variety of apple tree, characterized as to novelty by its similarity to the "Wealthy" variety while differing therefrom dominantly by its deeper over-all red color and earlier ripening season than "Wealthy" by some forty days, when grown under comparable conditions, substantially as shown and described.

EARL C. OHL.